United States Patent [19]

Weeks

[11] Plant 4,552

[45] Jun. 24, 1980

[54] ROSE PLANT

[76] Inventor: O. L. Weeks, 926 W. Philadelphia, Ontario, Calif. 91761

[21] Appl. No.: 1,709

[22] Filed: Jan. 8, 1979

Related U.S. Application Data

[63] Continuation of Ser. No. 845,239, Oct. 25, 1977, abandoned.

[51] Int. Cl.[2] ..... A01H 5/00

[52] U.S. Cl. ..... Plt./11

[58] Field of Search ..... Plt./11

*Primary Examiner*—Robert E. Bagwill
*Assistant Examiner*—James R. Feyrer
*Attorney, Agent, or Firm*—Frank B. Robb

[57] ABSTRACT

There is disclosed a new variety of rose of the hybrid tea class which is particularly distinguished by its unique purplish reddish to purplish pink tone, high centered flower of classic open formation, bordered by rim of ruby colored petals, distinct fragrance, larger, waxier foliage leaflets than its parent, Swarthmore, U.S. Plant. Pat. No. 2,444.

3 Drawing Figures

This application is a continuation of application Ser. No. 845,239 filed Oct. 25, 1977 now abandoned.

DESCRIPTION OF THE INVENTION

The present invention relates to a new and distinct variety of rose plant of the hybrid tea class, identified by me as #75-R-41, which I originated by crossing the seed parent "Swarthmore", U.S. Plant Pat. No. 2,444, with a pollen parent, being an unnamed seedling which I identify in my records as No. 64110-D-34, which was the result of a complicated series of crosses involving Angel Face, U.S. Plant Pat. No. 2,792, Sterling Silver, U.S. Plant Pat. No. 1,433, Circus, U.S. Plant Pat. No. 1,382 and Lavender Pinocchio, U.S. Plant Pat. No. 947, to perpetuate certain of the valuable aspects of each of the parents and endeavor to produce a new and distinct variety which has been in fact the result hereof.

As a result of this breeding I have produced this new and improved rose variety distinguished from its parents as well as from other rose varieties of which I am aware, as evidenced by the unique combination of principal characteristics set forth hereinafter and which are outstanding in the new variety:

(1) A very novel and distinctly different color, which is unique in my judgment, since it is a combination of purplish pink to purplish red edging the outer rim of petal;

(2) Large waxy foliage leaflets;

(3) High centered classic open flower formation with fewer petals than its seed parent;

(4) Fragrant distinct rose as compared with seed parent musky;

(5) Excellent growth habit for an outstanding garden rose with superior cutting ability.

Whereas the seed parent "Swarthmore" a deep, dusty pink color, the rose of my new variety is quite clearly and definitely a purplish pink with a contrasting purplish red border edging the outer rim of the petal.

Further contrast of the flowers of my new variety, disclose that they produce larger waxier foliage leaflets than "Swarthmore" and further are quite fragrant as compared with that parent.

Since the pollen parent is the result of a complex series of crosses, no one of them can be said to provide its greater influence except possibly the purplish pink aspect of Lavender Pinocchio which is much darker than that of the instant variety, and it does not include the purplish red edging of the petals of my new variety.

The seedling pollen parent is considerably smaller in flower form and less formal in conformation than the flowers of my variety, my new variety being a good growing plant.

Asexual reproduction of my new rose variety by budding as performed by me at Ontario, Calif. shows that the aforementioned characteristics and distinctions come true to form and are established and transmitted through succeeding propagations.

I am of the opinion that the new variety hereof is truly a novel and distinctively different rose than any other so-called lavender variety which to my knowledge is presently commercially grown.

My new rose variety appeals definitely to me as to its novelty and distinctiveness, and I believe that this would be true even to an untrained observer since it does involve the unique coloring and the classically formed bud with open flowers and distinct fragrance making it valuable as an outstanding garden rose and providing superior cutting ability.

The accompanying drawing shows typical specimens of the vegetative growth and flowers of my new variety displayed in different stages of development from the closed bud to the completely opened high centered flower as depicted in color as nearly true as it is reasonably possible to make the same in a color illustration of this character.

The following is a detailed description of my new variety, with color terminology in accordance with Nickerson Color Fan published by Munsell Color Company of Baltimore, Md., except where general color terms of ordinary dictionary significance are appropriate the observations having been made using incandescent daylight bulb lighting:

Type: Hardy; tall; bush; greenhouse or outdoor; seedling; for cut flowers and for garden decoration.

Class: Hybrid tea.

Breeding: Seedling.

*Seed parent.*—"Swarthmore" U.S. Plant Pat. No. 2,444.

*Pollen parent.*—An unnamed seedling identified as 64110-D-34.

Propagation: Holds its distinguishing characteristics through successive propagations by budding.

FLOWERS

Locality where grown and observed: Ontario, Calif.

Flowers borne: Occasionally singly, usually 4 to 5 in irregular pyramidal clusters with strong long stems.

Quantity of bloom: Abundant both outdoors and in the greenhouse.

Continuity: From intermittent to continuous.

Fragrance: Usually quite definite rose, but slightly musky.

Bud:

*Peduncle.*—Medium to long; medium caliper; erect; light yellowish to green bronze; somewhat rough; varying from few to numerous brown hairs.

*Before calyx breaks.*—Size — Medium to small. Form — Medium length; pointed; conspicuous neck; with foliaceous appendages on the surface of the bud; slender foliaceous parts extending beyond the tip of the bud equal to ½ to ¾ or more of its length. Color — Not significant.

*As calyx breaks.*—Color — Light pink at base blending into a deep red.

*As petals first open.*—Size — Small to medium. Form — Short to long and pointed. Color — Outside of bud — Petal somewhat lighter than dark red 5R3/7 blended with somewhat lighter than strong red 5R4/12. Inside of bud — Body of petal somewhat lighter than deep purplish pink 5RP6/10 blended with somewhat lighter than moderate purplish red 5RP5/11.

*Opening.*—Opens up well.

Bloom:

*Size (when fully open).*—3½ inches to 4½ inches.

*Petalage.*—Double; from 22 to 26 petals.

*Form.*—Full, high centered at first, becoming cupped; petals being at first tightly rolled inward; becoming rolled outward later; at maturity loosely cupped.

Petals:

*Texture.*—Moderately thick with inside shiney.

*Appearance.*—Inside shiny; outside satiny.

*Shape.*—Outside — Orbicular apex with bottom ovoid, with apex almost flat and 2 to 3 notches. Intermediate — Obovate; with apex flat with 1 to 2 notches. Inside — Between ovate and orbicular, with apex flat with 1 to 2 notches.

This description of a newly opened flower was made from a rose grown outdoors at Ontario, Calif.:

*Color.*—Outside petal — Outside surface — Body of petal a moderate purplish pink 2.5RP7/8 to strong purplish pink 7.5RP7/10. Inside surface — Body of petal light purplish pink near 2.5RP8/5 continuing into a pale lavender and a strong purplish red near 10RP4/12. Intermediate petal — Outside surface — From the lower portion the petal blends upward into and near a moderate purplish pink 10P7/7 and a deep purplish pink, near a strong reddish purple 10P4/10, the margin being overlayed with deep purplish pink 2.5RP6/10. Inside surface — Blending upward from lower portion into and near a deep purplish pink 7.5P8/5 and 10RP4/12, strong purplish red, the margin being overlayed with 2.5RP6/10 deep purplish pink. Inner petal — Outside surface — Body of petal pale purplish pink near 10P8/5. Inside surface — Blending upward from the lower portion into a pale purplish pink near 10P8/5 with margin more moderate purplish pink 2.5RP7/8.

This description was made from a rose that was opened for three days outdoors.

*Color.*—Outer petal — Outside surface — Blending upward from the lower portion into a moderate purplish pink 2.5RP7/8 with an occasional area of a moderate purplish red 5RP5/10. Inside surface — Blending upward from the lower portion into and between a light purplish pink 2.5RP8/5 and a moderate purplish pink 2.5RP7/8 and a top section of a strong purplish red 10RP4/12. Inside petal — Outside surface — The body of the petal is between a moderate purplish pink 10P7/7 and a moderate purplish pink 2.5RP7/8. Inside surface — The body of the petal at the bottom a deep purplish pink 5RP6/10 blending upward into a shade between a strong purplish pink RP4/12 and a strong purplish red 7.5RP5/12 including the margin.

*General color effect.*—Newly opened flower — A medium purplish reddish tone ranging from 10RP3/10 to moderate pink 10RP8/5. 3-days open — Generally and close to a strong purplish pink and light purplish pink in a color range from 7.5RP3/9 to 7.5RP8/5. Behavior — Drop off cleanly. Flower longevity — On bush in garden — 4 to 5 days in September; cut roses grown in the greenhouse kept at living room temperatures — 3 to 5 days in September.

REPRODUCTIVE ORGANS

Stamens: Many arranged irregularly about pistils, mixed with petaloids, tucked in calyx.

Filaments: Short to medium length; white; few; without anthers.

Anthers: Small; yellow and brown; open at various times.

Pollen: Moderate.

*Color.*—Lemon to gold yellow.

Pistils: Medium size.

Styles: Uneven; short to medium long length; very thin caliper; bunched and columnar.

Stigma: White.

Ovaries: All enclosed in calyx.

Hips: Oblong shaped; yellow green; very smooth; walls thin to thick and fleshy.

Sepals: Moderate to long; spear-shaped and curled.

Seeds: None observed.

PLANT

Foliage:

*Leaves.*—Compound of 5 to 7; abundant; medium size to large; moderately thin.

*Leaflets.*—Shape — Ovate with apex obtuse; margin doubly serrate. Appearance — more waxy than parent "Swarthmore".

*Color.*—Mature — Upper surface — Green with a touch of bronze. Under surface — Grey green with grey added. Young — Upper surface — Bronze. Under surface — Reddish green.

*Rachis (the supporting stem of the compound leaf).*—Medium weight. Upper side — Smooth. Under side — Somewhat thorny.

*Stipules.*—Short; narrow to medium width; short points turning out at an angle of 45 degrees.

*Disease and insect resistance.*—Normal to good resistance to powdery mildew and the usual rose insects under field grown conditions.

Growth:

*Habit.*—Tall; much branched.

*Growth.*—Vigorous.

*Canes.*—Heavy caliper.

*Main stems.*—Color — Green. Large prickles — Several; medium to long; hooked downward; with long narrow base. Color — Brown. Small prickles — None. Hair — None.

*Branches.*—Color — Bright yellowish green. Large prickles — Several; long; hooked downward with long narrow base. Color — Yellow. Small prickles — Brown. Hair — None. New shoots —

Color — Greenish bronze. Large prickles — Few; medium; hooked downward with long narrow base. Color — Red with yellow tips. Small prickles — Several. Color — Reddish. Hair — None.

I claim:

1. A new and distinct variety of rose plant of the hybrid tea class, substantially as herein shown and described, characterized particularly as to novelty by the purplish reddish high centered flower of classic open formation, bordered by a rim of strong purplish red colored petals, waxy foliage leaflets as compared with its parent "Swarthmore" U.S. Plant Pat. No. 2,444, distinct fragrance slightly musky, excellent growing characteristics as a garden and cutting flower.

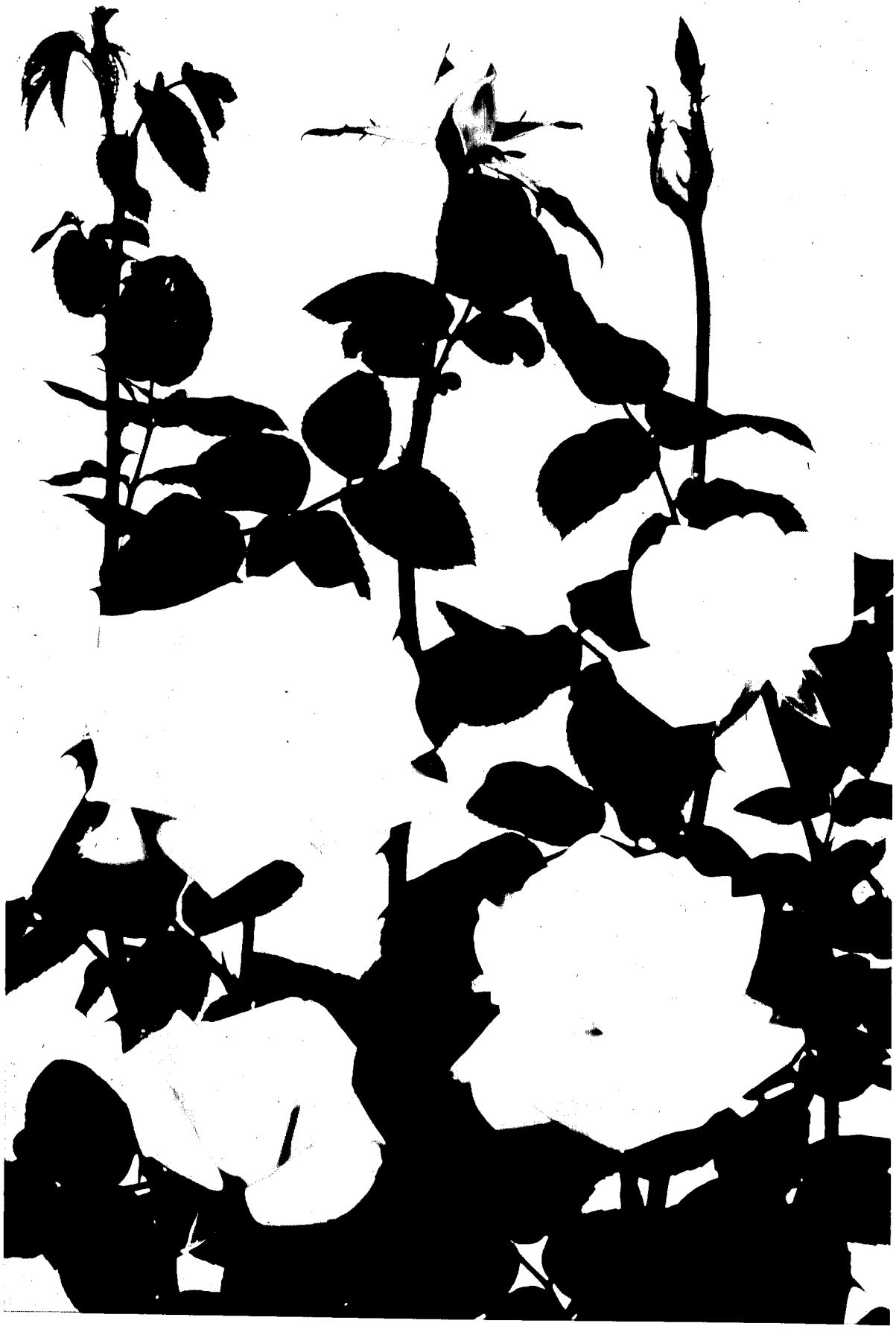

* * * * *